United States Patent [19]

Balderson et al.

[11] Patent Number: 5,849,594
[45] Date of Patent: Dec. 15, 1998

[54] CARBON DIOXIDE SENSITIVE MATERIAL

[75] Inventors: Simon Neville Balderson, Telford; Robert John Whitwood, Stafford; Andrew Mills; Lela Margaret Monaf, both of Swansea, all of Great Britain

[73] Assignee: Sealed Air (NZ) Limited, New Zealand

[21] Appl. No.: 836,910

[22] PCT Filed: Dec. 19, 1995

[86] PCT No.: PCT/GB95/02970

§ 371 Date: May 16, 1997

§ 102(e) Date: May 16, 1997

[87] PCT Pub. No.: WO96/19727

PCT Pub. Date: Jun. 27, 1996

[30] Foreign Application Priority Data

Dec. 19, 1994 [GB] United Kingdom .................... 9426053

[51] Int. Cl.$^6$ .................................................... G01N 33/50
[52] U.S. Cl. ................................ 436/133; 436/2; 422/85; 422/86; 128/205.28; 73/23.3
[58] Field of Search ............................ 422/58, 61, 83–88; 436/2, 133–134; 128/205.28; 73/23.3

[56] References Cited

U.S. PATENT DOCUMENTS 5,407,829  4/1995  Wolfbeis et al. ............................ 436/1

FOREIGN PATENT DOCUMENTS 0 449 798    10/1991   European Pat. Off. .
0 627 363    12/1994   European Pat. Off. .
WO 89/09078  10/1989   WIPO .
WO 91/05252  4/1991    WIPO .
WO 93/14399  7/1993    WIPO .

OTHER PUBLICATIONS

Mills, Andrew et al., Equilibrium Studies on Colorimetric Plastic Film Sensors for Carbon Dioxide, Anal. Chem. (1992), 64(13), 1383–9 Coden: Ancham;ISSN: 0003–2700, 1992.

*Primary Examiner*—Lyle A. Alexander
*Attorney, Agent, or Firm*—Bell Seltzer Intellectual Property Law Group of Alston & Bird LLP

[57] ABSTRACT

A carbon dioxide sensitive material including a polymer binder, a plasticiser, a lipophilic organic quaternary cation, an indicator dye anion and an aromatic alcohol in such concentration that the material changes color in accordance with the concentration of carbon dioxide.

11 Claims, No Drawings

CARBON DIOXIDE SENSITIVE MATERIAL

This invention relates to a carbon dioxide sensitive material for indicating whether a correct quantity of carbon dioxide has been flushed into a modified atmosphere package (MAP) and for indicating whether the concentration of carbon dioxide inside the package has diminished due to opening of or damage to the package.

In WO 91/05252 there is disclosed a carbon dioxide monitor which comprises a carbon dioxide sensitive material which changes colour in accordance with changes in concentration of carbon dioxide, the material comprising a lipophilic organic quaternary cation, an indicator dye anion, a polymer binder and a plasticiser. The concentration of carbon dioxide at which the materials change colour is generally below 5% and the material exhibits no further colour change when exposed to increased concentrations of carbon dioxide. The material is suitable for carbon dioxide monitoring in medical applications.

With modified atmosphere packaging, however, it is desired to monitor changes in concentrations of carbon dioxide in a package which are greater than 5%. For example, processed meat and fish are often packaged in an atmosphere containing 30% carbon dioxide, and red meat is often packaged in an atmosphere containing 100% carbon dioxide. The carbon dioxide sensitive materials known hitherto would be unsuitable for monitoring the concentration of carbon dioxide in MAP applications since such materials would change colour completely in an atmosphere containing 5% carbon dioxide, and a material in a package containing 5% carbon dioxide will exhibit the same colour as a material in a package containing 100% carbon dioxide.

It is desirable, therefore, to provide MAP with a carbon dioxide sensitive material which changes colour over a desired range of carbon dioxide concentrations.

According to the present invention there is provided a carbon dioxide sensitive material comprising a polymer binder, a plasticiser, a lipophilic organic quaternary cation, an indicator dye anion and an aromatic alcohol in such concentration that the material changes colour in accordance with concentration of carbon dioxide.

We have discovered that the colour of materials known hitherto changes significantly with temperature at constant carbon dioxide concentration. Consequently, it is impossible to determine the concentration of carbon dioxide unless the temperature is accurately known and, more importantly, unless the relationship between the temperature and the sensitivity of the material to carbon dioxide is known.

We have also discovered that known materials are more sensitive to carbon dioxide at lower temperatures than at higher temperatures. For example, at room temperature such a material might change colour when exposed to a 2% concentration of carbon dioxide, while at 0° C. the material will change colour when exposed to a 0.5% concentration of carbon dioxide.

We have also discovered that for known materials lower temperatures result in lower reaction speed; a material which changes colour within a few seconds at room temperature may take minutes at a temperature below 4° C.

Such a material would be unsuitable for a MAP application where it is desired to accurately sense a concentration of carbon dioxide in a package which is stored below 4° C. since sensitivity of the materials to carbon dioxide and speed of reaction to carbon dioxide are dependent on temperature.

Therefore, it is also desirable to provide MAP with a carbon dioxide sensitive material which is less sensitive to changes in temperature than materials known hitherto.

In accordance with the present invention the plasticiser is selected from the group of compounds comprising adipates, phthalates and phosphates so as to determine, in use, reaction speed and sensitivity of the material to temperature.

Following is a series of Tables indicating the factors that control the sensitivity towards carbon dioxide, the temperature sensitivity and the reaction speed of the material in accordance with the present invention.

It has been found that addition of aromatic alcohols to a conventional carbon dioxide sensitive material comprising a lipophilic organic quaternary cation, an indicator dye anion, a polymer binder and a plasticiser is effective for controlling the sensitivity of the material to carbon dioxide, that is to the sensitivity of the material to carbon dioxide, that is to say, for controlling the concentration of carbon dioxide at which the material undergoes a full colour change. We have found that suitable additives for this purpose include m-cresol, p-cresol, o-cresol, Santowhite ML (montedison), 2,4-dichlorophenol, 2-ethylphenol, 2-chlorophenol, 3-chlorophenol, 2-ethoxyphenol, phenol, resorcinol, naphthol, 2,6-dimethylphenol and 3,5-dimethylphenol.

Referring now to Table 1 below there is shown the relationship between the concentration of an aromatic alcohol additive and the carbon dioxide concentration at which a full colour change occurs. In this example the aromatic alcohol is the butylated reaction product of p-cresol and dichloropentadiene (Santowhite ML) and the indicator dye is m-cresol purple which changes colour from blue to yellow according to the concentration of carbon dioxide to which it is exposed.

TABLE 1

Effect of additive Santowhite ML on carbon dioxide sensitivity at a temperature of 0° C.

| Concentration of Santowhite ML (% of total dry film weight) | Concentration of carbon dioxide required to achieve a full yellow colour (% of final film weight) |
| --- | --- |
| 0 | 20 |
| 2 | 25 |
| 5 | 30 |
| 10 | 80 |
| 15 | 100 |
| 20 | >100 |

The table indicates that the concentration of carbon dioxode at which a full colour change occurs is proportional to the concentration of the aromatic alcohol additive (Santowhite ML) in the material.

Referring now to Table 2 below there is shown the relationship between the concentration in the material of another aromatic alcohol and the concentration of carbon dioxide required for a full colour change to occur. In this example the aromatic alcohol is m-cresol and the indicator dye is a mixture of m-cresol purple and cresol red which changes colour from blue to yellow.

TABLE 2

Effect of additive m-cresol on carbon dioxide sensitivity at a temperature of 0° C.

| Concentration of m-cresol (% of total dry film weight) | Concentration of carbon dioxide required to achieve a full yellow colour (% of final film weight) |
| --- | --- |
| 0 | 5 |
| 5 | 40 |
| 14 | 70 |
| 18 | >100 |

The Table indicates that the concentration of carbon dioxide at which a full colour change occurs is proportional to the concentration of the aromatic alcohol additive m-cresol.

In this example the change of colour occurs gradually and the material is seen to exhibit several colours as the concentration of carbon dioxide is increased from 0% to 100%. The actual colours depend upon the indicator dyes used in the formulation.

Referring now to Table 3 there is shown the range of colours exhibited by three indicator dyes; m-cresol purple, cresol red and phenol red.

TABLE 3

Colour range of indicator dyes sensitive to carbon dioxide at a temperature of 0° C.

| Indicator dye | Colour range |
| --- | --- |
| m-cresol purple | Blue - Green - Yellow |
| Cresol red | Purple - Brown - Orange - Red |
| Phenol red | Magenta - Red - Orange |

It will be appreciated that mixtures of these and other indicators sensitive to carbon dioxide can be used to give different colours and to extend the number of colours in the range of colours.

It will also be appreciated that the material will progressively exhibit a range of intermediate colours as the carbon dioxide concentration to which it is exposed is increased and that, as such, the actual colour of the material gives a direct indication of the carbon dioxide sensitivity to which the material is exposed.

Referring now to Table 4 there is shown colours exhibited by a carbon dioxide sensitive material in accordance with various concentrations of carbon dioxide. The indicator dye is cresol red and the aromatic alcohol additive is Santowhite ML at a concentration of 20% of dry film weight.

TABLE 4

Colour exhibited by the material at various carbon dioxide concentrations at a temperature of 0° C.

| Carbon dioxide concentration (% of final film weight) | Colour |
| --- | --- |
| 0 | Blue/purple |
| 20 | Brown |
| 30 | Buff |
| 40 | Mustard yellow |
| 70 | Matt yellow |
| 100– | Bright yellow |

It will be appreciated that two or more aromatic alcohol additives may be added to a carbon dioxide sensitive material.

It has been found that the sensitivity to temperature of carbon dioxide sensitive materials is a function of plasticiser type and, by selecting the plasticiser, sensitivity of the material to temperature can be reduced.

Referring now to Table 5 there is shown the relationship between plasticiser type and temperature sensitivity. Measurements for temperature sensitivity of the material were obtained by plotting the ratio of absorbance at 0% carbon dioxide to absorbance at concentrations of carbon dioxide up to 100%. Absorbance measurements were made at 600 nm over a range of temperatures from 0° C. to 40° C. The gradient ($\alpha$) of the curve at each temperature is obtained and an Arrhenius plot of $\ln(\alpha)$ vs. reciprocal temperature is constructed. The gradient of the Arrhenius plot is indicative of the sensitivity of the material to temperature. A lower value for the gradient indicates a lower sensitivity to temperature.

TABLE 5

Effect of plasticiser type on temperature sensitivity.

| Plasticiser type | Gradient of Arrhenius plot (×1000) |
| --- | --- |
| Di-isodecyl adipate | 6.259 |
| Di-isooctyl adipate | 5.533 |
| Di-2-ethylhexyl adipate | 6.195 |
| Di-(C7-9-alkyl) adipate | 5.362 |
| Butylbenzyl phthalate | 5.499 |
| 2-Ethylhexylbenzyl phthalate | 6.601 |
| Benzyl phthalate | 2.628 |
| Dimethyl phthalate | 3 808 |
| 2-Ethylhexyldiphenyl phosphate | 2.222 |
| Isodecyl phosphate | 3 523 |
| Tributyl phosphate | 6.510 |
| Tritolyl phosphate | 3.074 |
| Tris-2-ethyl phosphate | 3.747 |
| Castor oil | 5.116 |

It can be seen from the above table that the most effective plasticiser with regard to reducing temperature sensitivity is 2-Ethylhexyldiphenyl phosphate.

It has also been found that the carbon dioxide sensitivity of the material decreases with increasing plasticiser effectiveness. Thus the general order of decreasing carbon dioxide sensitivity with respect to plasticiser type is found to be adipate followed by phthalate followed by phosphate.

It has also been found that the speed at which the material reacts to presence of carbon dioxide is a function of plasticiser type and we have found that selection of plasticiser type and concentration of plasticiser in the material is critical to maintain an acceptable reaction speed at low temperature.

Referring now to Table 6 there is shown the relationship between plasticiser type, plasticiser concentration and the reaction speed.

TABLE 6

Effect of plasticiser type and concentration on the reaction speed at a temperature of 0° C.

| | Concentration of plasticiser | Time required to reach full colour at 100% |

| Plasticiser type | (% of dry film weight) | carbon dioxide (Seconds) |
|---|---|---|
| Santicizer 278 | 26 | 30 |
| Santicizer 278 | 31 | 15 |
| Santicizer 278 | 35 | 3 |
| Santicizer 141 | 26 | 15 |
| Santicizer 141 | 31 | 5 |
| Santicizer 141 | 35 | 5 |

The Table indicates that the reaction speed is dependent on the plasticiser type and the concentration of plasticiser in the material, the reaction speed generally becoming smaller with increasing concentration of plasticiser.

An effective plasticiser is taken to be one which reduces the response and recovery times of the material when exposed to an alternating atmosphere of 0–5% carbon dioxide. On this basis the most efficient plasticisers are phosphate-based, followed by phthalate- and then adipate-based plasticisers.

It will be appreciated that the material in accordance with the present invention may be used in a modified atmosphere package for the purpose of indicating correct packaging, package leakage, incorrect sealing or tamper evidence.

It will also be appreciated that the material may be used for the purpose of indicating directly the condition of a packaged product.

Furthermore, it will be appreciated that the material may be deposited on a micro-porous substrate and sealed onto an inner surface of a package.

That which is claimed is:

1. A carbon dioxide sensitive material comprising, in admixture, a polymer binder, a plasticiser, a lipophilic organic quaternary cation, an indicator dye anion and an aromatic alcohol in such concentration that the material changes colour in accordance with concentration of carbon dioxide.

2. The material as claimed in claim 1 wherein the aromatic alcohol is selected from the group consisting of 2,4-dichlorophenol, 2-ethylphenol, 2-chlorophenol, 3-chlorophenol, 2-ethoxyphenol, phenol, resorcinol, m-cresol, p-cresol, o-cresol, napthol, 2,6-dimethylphenol, 3,5-dimethylphenol, a butylated reaction product of p-cresol and dichloropentadiene, and mixtures thereof.

3. The material as claimed in claim 1 wherein the indicator dye anion is m-cresol purple, cresol red, phenol red or a mixture thereof.

4. The material as claimed in claim 1 wherein the indicator dye is adapted to exhibit a plurality of colours, each colour of which is indicative of a specific concentration of carbon dioxide.

5. A method for indicating directly the condition of a packaged product comprising exposing the carbon dioxide sensitive material of claim 1 to carbon dioxide in a package containing the product.

6. A method for indicating the concentration of carbon dioxide in a modified atmosphere package comprising exposing the carbon dioxide sensitive material of claim 1 to carbon dioxide in a modified atmosphere package.

7. A method for indicating the concentration of carbon dioxide in a package comprising the steps of:

depositing the carbon dioxide sensitive material of claim 1 on a micro-porous substrate; and sealing the micro-porous substrate to an inner surface of a package.

8. A package material adapted for use in modified atmosphere packaging, said package material having affixed thereon a microporous substrate, upon which is deposited the carbon dioxide sensitive material of claim 1.

9. A modified atmosphere package defined at least in part by a package material and comprising a modified atmosphere, a product exposed to said modified atmosphere, and the carbon dioxide sensitive material of claim 1 deposited on a microporous substrate and contained within or on said package material so as to contact said modified atmosphere.

10. The material as claimed in claim 1 wherein the plasticiser is selected from the group of compounds comprising adipates, phthalates and phosphates so as to determine, in use, reaction speed, sensitivity of the material to temperature and sensitivity of the material to changes in concentration of carbon dioxide.

11. The material as claimed in claim 10 wherein the plasticiser is either di-isodecyl adipate, di-isoctyl adipate, di-ethylhexyl adipate, di-(C7-9-alkyl) adipate, butylbenzyl phthalate, 2-ethylhexylbenzyl phthalate, benzyl phthalate, dimethyl phthalate, 2-ethylhexyldiphenyl phosphate, isodectyl phosphate, tributyl phosphate, tritolyl phosphate, tris-2-ethyl phosphate, castor oil or a mixture thereof.

* * * * *